United States Patent [19]

Escher et al.

[11] Patent Number: 5,276,152
[45] Date of Patent: Jan. 4, 1994

[54] PROCESS FOR THE PRODUCTION OF 4,6-DIALKOXYPYRIMIDINES

[75] Inventors: André Escher, Glis; Felix Previdoli, Brig, both of Switzerland

[73] Assignee: Lonza Ltd., Gampel/Valais, Switzerland

[21] Appl. No.: 6,524

[22] Filed: Jan. 21, 1993

[30] Foreign Application Priority Data

Jan. 23, 1992 [CH] Switzerland .................... 188/92

[51] Int. Cl.$^5$ .......................................... C07D 239/52
[52] U.S. Cl. ............................................... 544/319
[58] Field of Search ..................................... 544/319

[56] References Cited

U.S. PATENT DOCUMENTS 4,960,887 10/1990 Lachhein et al. ................. 544/320

FOREIGN PATENT DOCUMENTS 0024200 2/1981 European Pat. Off. .
0279366 8/1988 European Pat. Off. .
3939965 6/1991 Fed. Rep. of Germany .

OTHER PUBLICATIONS

Patent Abstracts of Japan, vol. 10, No. 328, (C-383) (2384), (Nov. 1986).
Prystas, Coll., Czech. Chem. Comm., vol. 32, (1967) pp. 4241 to 4259.
Shepherd et al., J. Org. Chem., vol. 26, No. 8, (Aug. 1961), pp. 2764 to 2769.
Shepard et al., Jr. Org. Chem., 26, (1961), pp. 2764 to 2769.
M. Prystas, Coll. Czech. Chem. Comm., 32, (1967), p. 4241.
K. Hartke and H. G. Muller, Arch. Pharm. (Weinheim), 321, (1988), pp. 863 to 871.
Muramatsu et al., Bull. Chem. Soc., Japan, 38 (1965), p. 244.

*Primary Examiner*—John M. Ford
*Attorney, Agent, or Firm*—Fisher, Christen & Sabol

[57] ABSTRACT

A process for the production of 4,6-dialkoxypyrimidines of the general formula:

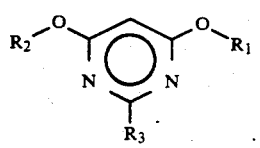

I

A propanediimidate of the general formula:

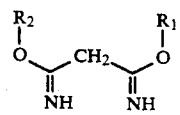

II is converted with an anhydride of the general formula:

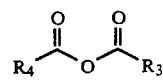

III to provide the product.

14 Claims, No Drawings

PROCESS FOR THE PRODUCTION OF 4,6-DIALKOXYPYRIMIDINES

BACKGROUND OF THE INVENTION

1. Field Of The Invention

The invention relates to a new process for the production of 4,6-dialkoxypyrimidines of the general formula:

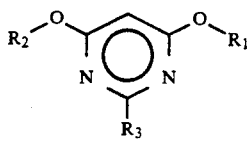

wherein $R_1$ and $R_2$ each means a $C_1$–$C_4$ alkyl group and $R_3$ means a hydrogen atom or a $C_1$–$C_4$ alkyl group, starting from a propanediimidate and an anhydride.

2. Background Art

The production of unsubstituted 4,6-dimethoxypyrimidine in the 2-position [Sheoherd et al., J. Org. Chem., 26, (1961), pp. 2764 to 2769] and the production of 2-methyl-4,6-dimethoxypyrimidine [M. Prvstas, Coll, Czech. Chem. Comm., 32, (1967), p. 4241] are known. In both of these processes, the corresponding 4,6-dialkoxypyrimidines, starting from 4,6-dichloropyrimidines, are produced by substitution with methylate. A great drawback of both of these processes lies in the fact that first the 4,6-dichloropyrimidines starting from the corresponding dihydroxypyrimidines have to be synthesized with chlorinated phosphate compounds, and large amounts of phosphate wastes result.

BROAD DESCRIPTION OF THE INVENTION

The main object of the invention is to eliminate these drawbacks and to provide a simple, ecologically and economically practicable process for the production of 2-substituted and 2-unsubstituted 4,6-dialkoxypyrimidines. Other objects and advantages of the invention are set out herein or are obvious herefrom to one skilled in the art.

The objects and advantages of the invention are achieved by the process of the invention.

The invention involves a process for the production of 4,6-dialkoxypyrimidines of the general formula:

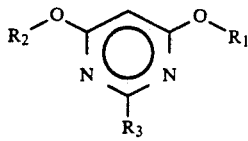

wherein $R_1$ and $R_2$ each is a $C_1$–$C_4$ alkyl group and $R_3$ is a hydrogen atom or a $C_1$–$C_4$ alkyl group. The process includes converting a propanediimidate of the general formula:

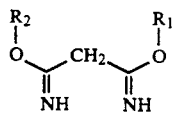

wherein $R_1$ and $R_2$ each has the above-mentioned meaning, with an anhydride of the general formula:

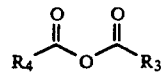

wherein $R_3$ has the above-mentioned meaning and $R_4$ is a $C_1$–$C_4$ alkyl group, into the product according to the general formula I.

The 4,6-dialkoxypyrimidines of general formula I can be converted by known reactions, e.g., by nitration with subsequent reduction, into 5-aminopyrimidines which, for example, represent important intermediate products for the production of herbicides (see European Published patent application No. 195,259).

DETAILED DESCRIPTION OF THE INVENTION

Propanediimidate, as feedstock for the process can be produced in a simple way starting from a propanediimidate dihydrochloride according to European Published patent application No. 024200. Propanediimidate dihydrochloride can be synthesized, e.g., in a simple way according to K. Hartke and H. G. Muller, Arch. Pharm. (Weinheim), 321, (1988), pp. 863 to 871.

Suitably, dimethyl-1,3-propanediimidate, wherein $R_1$ and $R_2$ each is a methyl group, is used as the propanediimidate for the process.

The anhydrides are commercially available or can be produced from the corresponding acid according to standard processes. If formyl acetate is used as anhydride for the process, the latter can be produced, for example, according to Muramatsu et al., Bull. Chem. Soc., Japan, 38, (1965), p. 244. The suitable anhydrides for the process are: formyl acetate, wherein $R_3$ is a hydrogen atom and $R_4$ is a methyl group, and acetic anhydride wherein $R_3$ and $R_4$ each is a methyl group.

Suitably the propanediimidate and the anhydride are used in equimolar amounts.

Suitably the reaction is performed in the presence of a base, such as, ammonia, or other amines, preferably in the presence of ammonia. The reaction suitably is performed at a temperature of 0° to 100° C., preferably of 0° to 40° C. Suitably the reaction is performed at a pH of 5 t 8, preferably of 6 to 7. As the solvent for the process, inert solvents, such as, diethyl ether, methylene chloride, acetonitrile, toluene or mixtures of these inert solvents, are suitable for the process. Preferably water immiscible solvents are used, such as, methylene chloride, diethyl ether or a mixture thereof.

After a usual reaction of 1 to 4 hours, the product according to the general formula I can then be worked up by methods usual to one skilled in the art.

EXAMPLE 1

4,6-Dimethoxypyrimidine 5.0 g of dimethyl-1,3-propanediimidate dihydrochloride was added by vigorous stirring to a mixture of 25 ml of $CH_2Cl_2$ and 25 ml of aqueous $K_2CO_3$ solution (300 g of $K_2CO_3/1$ solution). After 5 minutes the organic phase was separated and the aqueous phase was extracted with 10 ml of $Ch_2Cl_2$. The combined organic phases were dried on $Na_2SO_4$ and filtered. A freshly prepared mixture of 2.5 g of formyl acetate [produced from acetyl choloride and sodium formate according to Muramatsu et al., Bull. Chem. Soc., Japan, 38, (1965), p. 244] in 2 ml of diethyl ether was added at 0° C. to the above solution of the diimidate and stirred for two hours at this temperature. A small amount of ammonia gas was introduced (or ethereal ammonia solution was added) so that the reaction mixture showed an approximately neutral reaction with moistened pH paper. After another hour of stirring at 0° C., 10 ml of water was added. The organic phase was separated, dried on $Na_2SO_4$ and gently concentrated by evaporation. After distillation in a bulb tube furnace (product fraction: 110° C./16 mbar) the product was obtained as a colorless oil, which gradually solidified when allowed to stand. The yield of the product was: 2.4 g, which was 66.3 percent relative to the dihydrochloride used with a product content of 96 percent (GC).

EXAMPLE 2

4,6-Dimethoxy-2-methylpyrimidine

As in Example 1, 5 g of dimethyl-1,3-propanediimidate dihydrochloride was released and taken up in $Ch_2Cl_2$. After addition of 2.6 g of acetic anhydride, the solution was refluxed for two hours. After addition of $NH_3$ up to neutral reaction with moistened pH paper, the solution was refluxed another hour, allowed to cool and 5 ml of water was added. After distilling off $Ch_2Cl_2$ on a rotary evaporator, the precipitated product was filtered off, washed with a little water and dried at room temperature to 26 mbar. 2.2 g of white crystalline product (melting point: 51° to 52° C.) with a content of 98 percent (GC) was obtained, which corresponded to a yield of 56.3 percent relative to the dihydrochloride. By extraction of the aqueous phase and subsequent column chromatography it was possible to raise the yield to 68 percent.

What is claimed is:

1. A process for the production of a 4,6-dialkoxypyrimidine

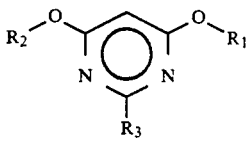

wherein $R_1$ and $R_2$ each is a $C_1$–$C_4$ alkyl group and $R_3$ is a hydrogen atom or a $C_1$–$C_4$ alkyl group, comprising converting a propanediimidate of formula:

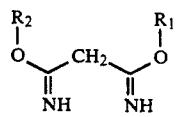

wherein $R_1$ and $R_2$ have the above-mentioned meaning, with an anhydride of formula:

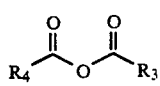

wherein $R_3$ has the above-mentioned meaning and $R_4$ is a $C_1$–$C_4$ alkyl group, into the 4,6-dialkoxypyrimidine according to formula I.

2. The process according to claim 1 wherein dimethyl-1,3-propanediimidate, wherein $R_1$ and $R_2$ each is a methyl group, is used as the propanediimidate of the formula II.

3. The process according to claim 2 wherein either formyl acetate, wherein $R_3$ is a hydrogen atom and $R_4$ is a methyl group, or acetic anhydride, wherein $R_3$ and $R_4$ each is a methyl group, is used as the anhydride of formula III.

4. The process according to claim 3 wherein the conversion is performed at a temperature of 0° to 100° C.

5. The process according to claim 1 wherein either formyl acetate, wherein $R_3$ is a hydrogen atom and $R_4$ is a methyl group, or acetic anhydride, wherein $R_3$ and $R_4$ each is a methyl group, is used as the anhydride of formula III.

6. The process according to claim 1 wherein the conversion is performed at a temperature of 0° to 100° C.

7. The process according to claim 1 wherein the conversion is conducted at a pH of 5 to 8.

8. A process for the production of a 4,6-dialkoxypyrimidine of formula:

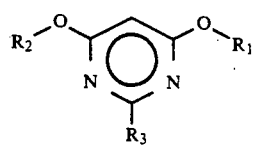

wherein $R_1$ and $R_2$ each is a $C_1$–$C_4$ alkyl group and $R_3$ is a hydrogen atom or a $C_1$–$C_4$ alkyl group, comprising converting a propanediimidate of formula:

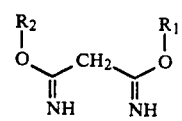

wherein $R_1$ and $R_2$ have the above-mentioned meaning, with an anhydride of formula:

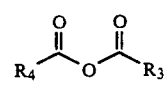

wherein $R_2$ has the above-mentioned meaning and $R_4$ is a $C_1$–$C_4$ alkyl group, in the presence of a base, into the 4,6-dialkoxypyrimidine according to formula I.

9. The process according to claim 8 wherein the base is ammonia or an amine.

10. A process for the production of a 4,6-dialkoxypyrimidine of formula:

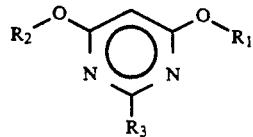

wherein $R_1$ and $R_2$ each is a $C_1$–$C_4$ alkyl group and $R_3$ is a hydrogen atom or a $C_1$–$C_4$ alkyl group, comprising converting a propanediimidate of formula:

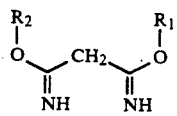

II wherein $R_1$ and $R_2$ have the above-mentioned meaning, with an anhydride of formula:

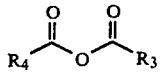

III wherein $R_2$ has the above-mentioned meaning and $R_4$ is a $C_1$–$C_4$ alkyl group, in the presence of an inert solvent, into the 4,6-dialkoxypyrimidine according to formula I.

11. The process according to claim 10 wherein the inert solvent is selected from the group consisting of diethyl ether, methylene chloride, acetonitrile, toluene and a mixture of at least two of said inert solvents.

12. The process according to claim 10 wherein dimethyl-1,3-propanediimidate, wherein $R_1$ and $R_2$ each is a methyl group, is used as the propanediimidate of the formula II.

13. The process according to claim 10 wherein either formyl acetate, wherein $R_3$ is a hydrogen atom and $R_4$ is a methyl group, or acetic anhydride, wherein $R_3$ and $R_4$ each is a methyl group, is used as the anhydride of formula III.

14. The process according to claim 10 wherein the conversion is performed at a temperature of 0° to 100° C.

* * * * *